United States Patent [19]
Wilson et al.

[11] Patent Number: 4,816,448

[45] Date of Patent: Mar. 28, 1989

[54] THERMAL ISOMER OF DIFFICIDIN AND THERMAL ISOMER OF OXYDIFFICIDIN ANTIBACTERIALS

[75] Inventors: Kenneth E. Wilson, Westfield; James E. Flor, Bridewater; Otto D. Hensens, Red Bank; Jerrold M. Liesch, Princeton Junction; Reamer, Robert A., Bloomfield, all of N.J.

[73] Assignee: Merck & Co., Inc., Rahway, N.J.

[21] Appl. No.: 11,189

[22] Filed: Feb. 5, 1987

[51] Int. Cl.$^4$ .................... A61K 31/665; C07F 9/09
[52] U.S. Cl. ..................................... 514/99; 549/222
[58] Field of Search .......................... 549/222; 514/99

[56] References Cited

U.S. PATENT DOCUMENTS 4,545,991  10/1985  Zimmerman et al. ............ 514/99

*Primary Examiner*—Richard L. Raymond
*Attorney, Agent, or Firm*—Richard S. Parr; Hesna J. Pfeiffer

[57] ABSTRACT

The present invention relates to novel antibacterial compounds referred to herein generally as a thermal isomer of difficidin and thermal isomer of oxydifficidin. Also disclosed is process for preparing, isolating and purifying said compounds.

5 Claims, 2 Drawing Sheets

THERMAL ISOMER OF DIFFICIDIN AND THERMAL ISOMER OF OXYDIFFICIDIN ANTIBACTERIALS

BACKGROUND OF THE INVENTION

Field of the Invention

The present invention relates to novel antibacterial compounds referred to herein generally as a thermal isomer of difficidin and thermal isomer of oxydifficidin. Also disclosed is process for preparing, isolating, and purifying said compounds. As employed herein, the term "thermal isomer of difficidin" refers to the compound (Z,Z,E,Z,Z,)-16-dihydroxyphosphinoxy-5,7-dimethyl-4-methylene-22-((E)-3-methyl-3,5-hexadienyl-)oxacyclo-docosa-8,10,12,17,19-pentaen-2-one, which has the structural formula as described in Formula II, hereinbelow, wherein $R^1$ is hydrogen, and $R_a$ and $R_b$ have the recited meanings, thus affording various salt forms thereof. Corresponding, the term "thermal isomer of oxydifficidin", as used herein, refers to the compound (Z,Z,E,Z,Z,)-16-dihydroxy-phosphinoxy-5,7-dimethyl-6-hydroxy-4-methylene-22-((E)-3-methyl-3,5-hexadienyl)oxacyclodocosa-8,10,12,17,19-pentaen-2-one, which has the structural formula as described in Formula II, hereinbelow, wherein $R^1$ is hydroxy, and $R_a$ and $R_b$ have the indicated meanings. The novel antibacterial compounds can be obtained by microbiological cultivation of *Bacillus subtilis*, MB 3575 or MB 4488 deposited with the American Type Culture Collection, Rockville, Md. under the designations ATCC 39374 and 39320, respectively.

The noval antibacterial compounds of the present invention are broad spectrum antibacterials with good potency against aerobic microorganisms and exceptional potency against anaerobic microorganisms. They also exhibit good in vitro activity against microorganisms that have developed resistance to conventional antibacterials. They may be used parenterally in the treatment of gram positive and gram negative bacterial infections.

BRIEF DESCRIPTION OF THE PRIOR ART

Difficidin and oxydifficidin are known antibacterial agents and have the following formula:

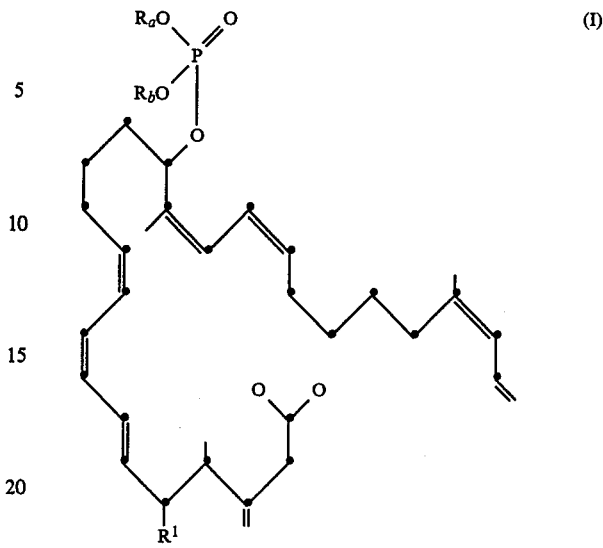

where $R_a$ and $R_b$ are members independently selected from the group consisting of hydrogen, alkali metal and alkaline earth metal cations, ammonium, and substituted ammonium, and $R^1$ is hydrogen or hydroxy. Difficidin is present when $R^1$ is hydrogen and oxydifficidin is present when $R^1$ is hydroxy. Difficidin and oxydifficidin can be obtained by the microbiological cultivation of *Bacillus subtilis* ATCC 39374 or 39320. Thus, difficidin and oxydifficidin and the compounds of the subject invention, i.e. the thermal isomer of difficidin and thermal isomer of oxydifficidin, are co-produced by the cultivation of *Bacillus subtilis* ATCC 39374 and 39320. A complete description of difficidin and oxydifficidin can be found in U.S. Pat. No. 4,545,991.

Although the structural formula of difficidin and the thermal isomer of difficidin are closely related and the structural formula of oxydifficidin and the thermal isomer of oxydifficidin are closely related, it is believed that it is easier to chemically modify the thermal isomer in order to obtain what is commonly referred to as a "semi-synthetic" antibacterial agent.

Proticin is a known antibacterial compound which has been described as a phosphorous-containing, strongly unsaturated amorphous compound with broad activity spectrum, especially against gram negative pathogens. It is said to have been produced by fermentation of a strain identified as a form of *Bacillus licheniformis*. A more detailed description of its preparation, characteristics, and anti-bacterial activity can be found in the following references: (1) Präve, P. et al., J. Antibiotics 25 (1): 1–3, 1972; (2) Vertesy, L., J. Antibiot. 25 (1): 4–10, 1972; (3) Nesemann, G., et al., Naturwissenschaften 59 (2): 81–82, 1972; (4) Ger. Offen. No. 2,035,812 (Vertesy. L. et al.), "Proticin from *Bacillus licheniformis*", Farbwerke Hoechst A.-G., July 18, 1970; and (5) Brit. No. 1,350,271, "Proticin Production by *Bacillus licheniformis* fermentation," Farbwerke Hoechst A.-G., Apr. 18, 1974. (ref. Chem. Abstracts 81: 48531y, p. 30b, 1974).

However, despite the repeated reference to the specific antibiotic compound proticin, the above references fail to characterize any single compound, and the spectral data provided therein is consistent with a number of possible compounds. Since Vertesy Reference (2) above describes the presence of a methyl group at only one of the double bonds, whereas the compounds of the present invention have two such methyl groups, it has been concluded that the novel antibacterial compound of the present invention, wherein $R^1$ is hydroxy (thermal isomer of oxydifficidin) is chemically distinct from the so-called proticin, described in the above references. On the other hand, the novel antibacterial compound of the present invention wherein $R^1$ is hydrogen (thermal isomer or difficidin) is readily distinguished from the compound(s) of the references since it has a different molecular weight.

As can be seen, there are two chief compounds within Formula II, hereinbelow. One compound is that wherein $R^1$ is hydrogen, which as already mentioned, shall be referred to hereinafter as the "thermal isomer of difficidin"; and the other compound is that wherein $R^1$ is hydroxy, which shall be referred to hereinafter as the "thermal isomer of oxydifficidin".

Biologically, the thermal isomer of difficidin has been found to be more potent than the thermal isomer of oxydifficidin against aerobic microorganisms such as *Pseudomonas aeruginosa* and *Staphylococcus aureus*. In most cases it was found to be four times more effective against *S. aureus, Ps. aeruginosa, Salmonella typhimurium*, Proteus, and *Serratia marcescens* than the thermal isomer of oxydifficidin. The thermal isomer of difficidin and thermal isomer of oxydifficidin are also active against a wide spectrum of anaerobic bacteria.

DETAILED DESCRIPTION OF THE INVENTION AND PREFERRED EMBODIMENTS

Figure 1:
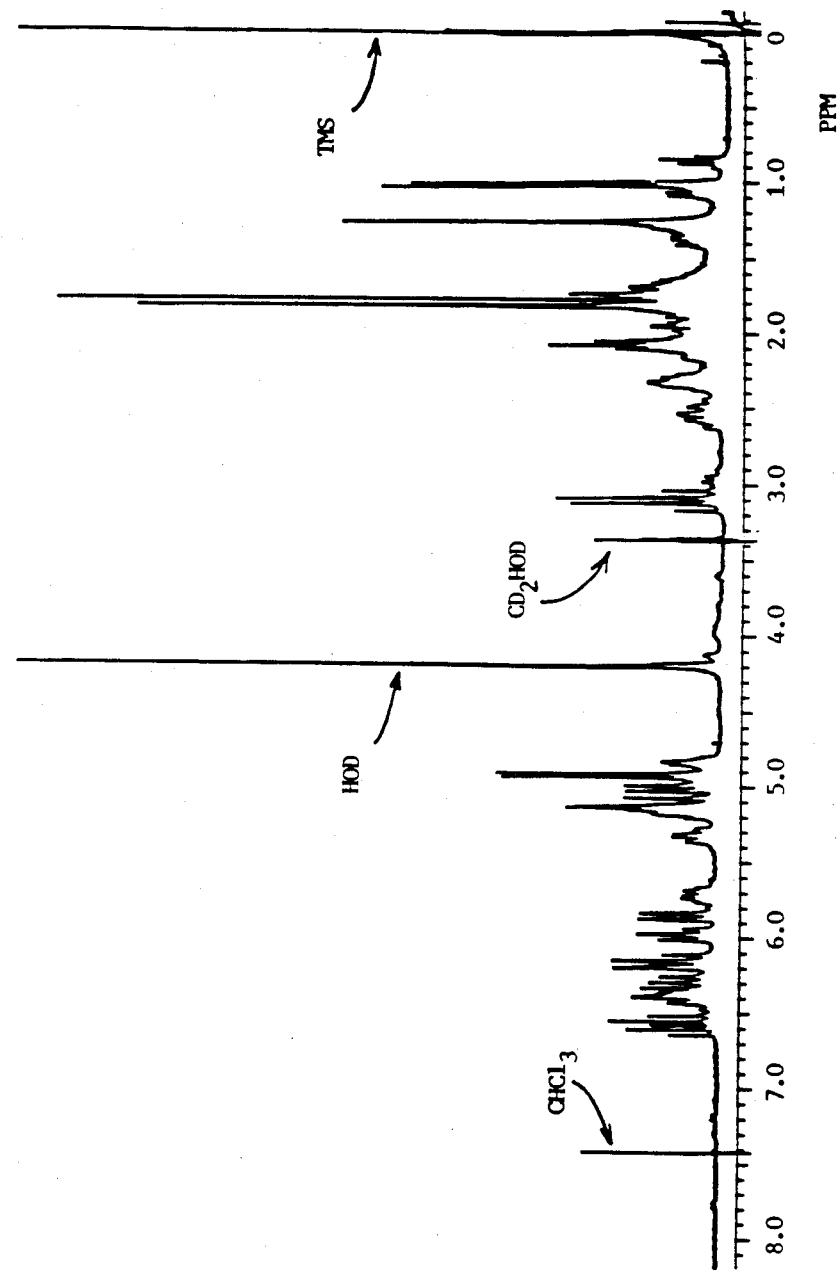

In accordance with the present invention there is provided a thermal isomer of difficidin and a thermal isomer of oxydifficidin of the formula:

(II)

where $R_a$ and $R_b$ are members independently selected from the group consisting of hydrogen, alkali metal and alkaline earth metal cations, ammonium and substituted ammonium and $R^1$ is hydrogen or hydroxy.

The ammonium cation may be substituted in known manner, preferably with lower alkyl, for example.

The thermal isomers of the subject invention have been prepared and utilized as the potassium phosphate salt, being a changing equilibrium of the mono- and di-potassium salts. This salt form has been employed due to its ease of preparation and the possible instability of the acid form, where $R_a = R_b = H$, which exists at a low pH.

The thermal isomers of the subject invention can be prepared by microbiological cultivation of *Bacillus subtilis*, MB 3575 or MB 4488 deposited with the American Type Culture Collection, Rockville, Md., from which it is available without restriction under the accession numbers ATCC 39374 and 39320, respectively. It should be noted that the *Bacillus subtilis* ATCC 39374 and ATCC 39320 can be cultivated to produce the thermal isomers of the subject invention by the same techniques as those described in U.S. Pat. No. 4,545,991.

The bacillus or its variants and mutants can be cultivated in accordance with well known microbiological processes, either on agar slant tubes or under submerged conditions in Erlenmeyer flasks or fermentors, utilizing nutrient media or nutrient solutions generally employed for cultivating microorganisms.

In the present invention, the thermal isomer of difficidin and thermal isomer of oxydifficidin are produced during cultivation of the microorganism, for example, *Bacillus subtilis* ATCC 39320 at a temperature of about 28° C., under aerobic conditions. The composition of the nutrient medium can be varied over a wide range. The essential assimilable nutrient ingredients are; a carbon source, a nitrogen source, a source of inorganic elements including phosphorus, sulfur, magnesium, potassium, calcium and chlorine. Cultivation is most productive under neutral pH conditions, preferably from about 6.0 to about 7.0.

Typical sources of carbon include, glucose, dextrin, starches, glycerol and the like. Typical nitrogen sources include vegetable meals (soy, cottonseed, corn, etc.), meat flours or animal peptones, distillers solubles, casamino acids, yeast cells, various hydrolysates (casein, yeast, soybean, etc.), yeast nucleic acids and amino acids.

Mineral salts such as the chlorides, nitrates, sulfates, carbonates and phosphates of sodium, potassium, ammonium, magnesium and calcium provide a source of essential inorganic elements. The nutritive medium may also contain a number of trace elements such as iron, copper, manganese, zinc and cobalt.

If excessive foaming is encountered during the cultivation, antifoaming agents such as vegetable oils, lard oil and polypropylene glycol may be added to the fermentation medium prior to, or during the course of the fermentation. Satisfactory yields of the thermal isomers of the subject invention can be achieved within from about 20 to about 120 hours, and is culture dependent. The inoculum for the fermentation can be provided from suspensions, slants, frozen cells or freeze-dried preparations.

In addition to the conventional cultivation process described hereinabove, there may also be employed continuous processes, such as that described in *Methods in Microbiology*, Vol. 2, Academic Press, London—N.Y., 1970, pp. 259–328. In such systems the bacillus can be maintained for extended periods of time in a steady state without spontaneous mutations or other degenerations becoming evident.

It is to be understood that for the production of the thermal isomers of the subject invention, the subject invention is not limited to the use of *Bacillus subtilis* ATCC 39374 or 39320. It is especially desired and intended to include the use of natural or artificial mutants produced from the described organisms, or other variants of *Bacillus subtilis* ATCC 39374 or 39320 as far as they can produce the thermal isomer of difficidin and the thermal isomer of oxydifficidin. The artificial production of mutant *Bacillus substilis* can be achieved by a conventional operation such as X-ray or ultraviolet (UV) radiation, or by the use of chemical mutagens such as; nitrogen mustards, nitrosoguanidine, camphor and the like, or by means of recombinant DNA technology.

Alternatively, the thermal isomers of the subject invention can be prepared by converting difficidin and oxydifficidin to the thermal isomer of difficidin and thermal isomer of oxydifficidin, respectively. Difficidin and oxydifficidin can be prepared and purified as described in U.S. Pat. No. 4,545,991. The thermal isomers can be prepared by thermally heating (to about 60° C.) the difficidin and oxydifficidin in a suitable solvent system such as water, alcohol or ethyl acetate. At 60° C., it takes about 24 hours for difficidin and oxydifficidin to reach equilibrium with its thermal isomer. At equilibrium, about 25% of the difficidin has converted to the thermal isomer and about 66% of the oxydifficidin has converted to its thermal isomer. It should be noted that at room temperature some isomerization takes place. The thermal isomer can then be separated from the equilibrium mixture by standard chromatographic techniques.

MORPHOLOGICAL AND PHYSIOLOGICAL CHARACTERISTICS OF BACILLUS SUBTILIS ATCC 39320

The morphological and physiological properties of ATCC 39320 are as follows:
Morphology: gram positive, non-vacuolated vegetative rods with rounded ends; average size $0.9 \times 2.3-3.6\mu$; occurring singly. Rods are motile. Spores are produced under aerobic conditions. Spores are $0.5 \times 1.0\mu$ (average size), oval to cylindrical, predominantly central, sporangia not swollen.
Colonial appearance: flat, found with irregular edge, surface dull, edge becoming opaque as colony ages. Dull, wrinkled entire pellicle on surface of broth. No pigmentation on trypticase soy agar. Growth at 28° C., 37° C., no growth at 60° C.
Positive reactions: Catalase, Voges-Proskauer, gelatin, nitrate reduction, utilization of citrate, acid from glucose, arabinose, mannitol, xylose, sorbitol and sucrose, hydrolysis of starch.
Negative reactions: urease, indole, utilization of propionate, arginine dihydrolyase, acid from rhamnose and mellibiose, no growth in anaerobic agar (stabs or plates incubated in anaerobic jars), no growth in glucose broth or nitrate broth under anaerobic conditions.

Comparison with culture descriptions in Bergey's *Manual of Determinative Bacteriology*, Eighth Edition, Williams & Wilkins, 1974, and Gordon, R. E., Haynes, W. C. and Pang, C. H. (1973), The Genus *Bacillus*, Agriculture Monograph No. 427, U.S. Department of Agriculture, Washington, D.C., indicate that MB 4488/ATCC 39320 is a strain of known species *Bacillus substilis*.

MORPHOLOGICAL AND PHYSIOLOGICAL CHARACTERISTICS OF BACILLUS SUBTILIS ATCC 39374

The morphological and physiological properties of ATCC 39374 are the same as those indicated above for ATCC 39320, except with respect to the appearance of the colonies of the microorganism, which are as follows:
Colonial appearance: At 24 hours, raised, round, mucoid. As colony ages, edge becomes dry, opaque and irregular. Central mucoid area continues to dry, becoming opaque and wrinkled. Dull, wrinkled entire pellicle on surface of broth. No pigmentation on trypticase soy agar. Growth at 28° C., 37° C., no growth at 60° C.

PRODUCTION OF THE THERMAL ISOMER OF DIFFICIDIN AND THERMAL ISOMER OF OXYDIFFICIDIN

A. A process for preparing the thermal isomer of difficidin of the invention and the thermal isomer of oxydifficidin of the invention, or one of their salts, but in which the thermal isomer of oxydifficidin is produced in greater proportion, involves the cultivation of microorganisms which form the thermal isomers of the subject invention and belong to the strain of *Bacillus subtilis* ATCC 39320 at a temperature ranging from 20° C. to 40° C. for from 24 to 120 hours by means of an aqueous nutrient solution which contains a source of carbon, a source of nitrogen, nutrient salts and trace elements, until the nutrient solution contains considerable amounts of the thermal isomer of difficidin and the thermal isomer of oxydifficidin, after which such thermal isomers are isolated from the culture and converted, if desired, into a salt with a pharmaceutically acceptable base.

During cultivation the pH value of the nutrient medium changes from neutral to slightly acidic. In general the addition of a buffer solution is not necessary, although one could be employed as a precaution. The cultivation is suitably stopped after 2 to 4 days, since a favorable yield is obtained after this period; the nutrient solution then contains a substantial amount of the thermal isomer oxydifficidin.

B. Another process for preparing the thermal isomer of difficidin of the invention and thermal isomer of oxydifficidin of the invention, or one of their salts with a pharmaceutically acceptable base involves the cultivation of microorganisms which form the thermal isomers of the subject invention and belong to the strain of *Bacillus subtilis* ATCC 39374 at a temperature ranging from 20° C. to 40° C. for from 24 to 120 hours by means of an aqueous nutrient solution which contains a source of carbon, a source of nitrogen, nutrient salts and trace elements, including particularly cobalt, until the nutrient solution contains considerable amounts of the thermal isomers after which the thermal isomers are isolated from the culture and converted, if desired, into a salt with a pharmaceutically acceptable base.

ISOLATION OF THE THERMAL ISOMER OF DIFFICIDIN AND THE THERMAL ISOMER OF OXYDIFFICIDIN

In order to isolate the thermal isomer of difficidin of the invention and the thermal isomer of oxydifficidin of the invention the culture of the bacillus may first be clarified by centrifugation, which, however, results in a considerable proportion of such thermal isomers remaining in the cell mass. This crude product can be purified in order to obtain the thermal isomers by chromatography using an appropriate adsorbent such as polymeric organic based resins, such as Dowex-1, XAD-2 and HP-20 resins, and polymeric silicic acid based resins, such as LiChroprep RP-18 resin and Watman ODS resins, both of which are silica with a chemically bonded outer layer of $C_{18}H_{37}$ residues.

ANTIBACTERIAL ACTIVITY

Using standard in vitro assay techniques, minimal inhibitory concentrations (MIC) have been determined for the thermal isomer of difficidin and the thermal isomer of oxydifficidin against a number of bacteria. The results obtained are illustrated in Table I below.

TABLE I

| | MIC ($10^4$ μg/ml) | |
|---|---|---|
| Aerobic Bacteria | Thermal Isomer Oxydifficidin | Thermal Isomer Difficidin |
| *Staphylococcus aureus* Gm ® Meth ® | >128.0 | — |
| *S. aureus* | >128.0 | — |
| *S. aureus* | 128.0 | 128.0 |
| *S. aureus* | — | >128.0 |
| *Streptococcus faecalis* | >128.0 | — |
| *S. faecalis* | — | 4.0 |
| *Escherichia coli* TEM 2+ | 32.0 | — |
| *E. coli* TEM 2+ DC 2 | 32.0 | — |
| *E. coli* DC 2 | 32.0 | — |
| *E. coli* | 32.0 | 8.0 |
| *E. coli* | — | 4.0 |
| *Salmonella typhimurium* | 32.0 | — |
| *Enterobacter cloacae* P99+ | 32.0 | 8.0 |
| *E. cloacae* P99− | 32.0 | — |
| *E. aerogenes* | >128.0 | 16.0 |
| *Klebsiella pneumoniae* K1+ | 64.0 | — |
| *K. pneumoniae* | >128.0 | 4.0 |
| *Proters vulgaris* | 32.0 | 2.0 |
| *P. morganii* Sm ® | 8.0 | 2.0 |
| *P. mirabilis* Gm ® | 32.0 | 4.0 |
| *Pseudomonas aeruginosa* RPL 11+ | 64.0 | — |
| *P. aeruginosa* | 128.0 | 16.0 |
| *P. aeruginosa* | 128.0 | — |
| *P. aeruginosa* | — | 8.0 |
| *Serratia marcescens* | 64.0 | 8.0 |

From the foregoing in vitro data it is expected that an effective antibacterial amount of thermal isomer of difficidin and thermal isomer of oxydifficidin would be on the order of 5 mg/kg to 20 mg/kg in mammals. Such thermal isomers are effective for treatment of gram negative and gram positive infections as described above, and may be administered intravenously, intramuscularly, or subcutaneously, either alone or in combination with a pharmaceutical carrier. The ultimate choice of route and dose should be made by an attending physician and based upon the patient's unique condition.

Combinations of the thermal isomers of the subject invention with appropriate pharmaceutical carriers are accomplished by methods well known to the pharmacist's art. For purposes of subcutaneous (s.c.) administration, solutions of the thermal isomer of difficidin and thermal isomer of oxydifficidin are generally employed, for example, sterile aqueous or alcoholic solutions. Such solutions should be suitably buffered if necessary and the liquid diluent may first be rendered isotonic with saline or glucose. These aqueous and alcoholic solutions are also suitable for intravenous (i.v.) injections.

The following examples illustrate the preparation and isolation of the thermal isomer of difficidin and the thermal isomer of oxydifficidin from *Bacillus subtilis* ATCC 39320 and ATCC 39374.

EXAMPLE I

Fermentation Production of Thermal Isomer of Difficidin

1. Inoculum Development B-Flask Laboratory Stage

The culture MB3575 is used to inoculate a 250 ml baffled Erlenmeyer flask containing 50 ml of HSM-1 medium. This flask is incubated for 12 hours at temperature 28° C. on the rotary shaker at 220 RPM.

C-Flask Laboratory Stage

Fifteen ml of fermentation broth from "B" flask is used to inoculate a 2.0 liter baffled Erlenmeyer flask containing 500 ml of HSM-1 medium with presterile pH=6.8. These flasks are incubated for 12 hours at a temperature of 28° C. on the rotary shaker at 220 RPM.

HSM-1 Seed Medium is as follows:

| Components | g/l |
|---|---|
| Yeast extract (Difco) | 1.0 |
| Malt extract (Difco) | 1.0 |
| Beef extract (Difco) | 1.0 |
| Trypticase Peptone (Difco) | 25.0 |
| Trypticase Soy (Difco) | 0.1 |
| Glucose | 5.0 |
| Soybean Oil | 0.1 |
| Corn Steep Liquor | 0.5 |
| Calcium Carbonate ($CaCO_3$) | 10.0 |
| Sucrose | 10.0 |
| Soybean flour | 10.0 |
| Soluble starch | 10.0 |

The medium is prepared with distilled water. No pH adjustment is required. 40 ml medium in "B" flask and 500 ml in C flask are sterilized for 20 minutes at 121° C.

Production Stage

The production stage was conducted in an "E" scale (800 liters) fermentor with 550 liters volume for cultivation.

The medium used is:

| Components | Concentration g/l | Charge Amount |
|---|---|---|
| Industrial Starch 3005 | 60 | 33 kg |
| Solulac | 10.5 | 5.77 kg |
| Ardamine YEP | 7.5 | 4.125 kg |
| Cobalt chloride ($CoCl_2\ 6H_2O$) | 0.15 | 0.082 kg |
| Potassium Phosphate Monobasic | 0.21 | 0.115 kg |
| Noro-Termamyl-120αamylase | 0.073 ml/L | 40 ml |
| Polyglycol P-2000 | 0.7 ml/L | 385 ml |

The batching procedure is as follows: The industrial starch 3005 and DI water were charged to the "E" scale fermentor and 40 ml of Novo-Termamyl-120αamylase was added. The starch suspension was agitated and heated up to 90° C. for 40 minutes to solubilize the starch enzymatically. After this period the tank was cooled down to 600° C. and the rest of the ingredients were charged. Volume was adjusted to 550 liters by adding water: the pH was adjusted to 7.2 with NaOH solution before sterilization.

The medium was sterilized for 20 minutes at 121° C.

The fermentor was inoculated with two "C" flasks and cultivated during 120 hours at the following conditions:

Temperature, 28° C.
Air flow, 150 LPM (0.27 vvm)
Agitation, 200 RPM
Pressure, 0.7 kg/cm2
Defoamer was added as needed to control foam.

EXAMPLE II

Isolation of Thermal Isomer of Difficidin

Harvesting of the fermentation batch of Example I provided 450 L of whole broth with a difficidin titer of 160 mg/L and an oxydifficidin titer of 90 mg/L. The whole broth was diluted with 190 L of isopropanol. The mixture was clarified using a Sharples centrifuge. The clarified broth was adsorbed batchwise onto 45 L Dowex 1×2 (chloride) resin. The spent broth was decanted and the resin was washed with 90 L of distilled water. The resin was transferred to a column (10" ID) and the antibiotic complex was eluted from the resin with 200 L of 3% ammonium chloride in 9:1 methanol-water, downflow at 4 L/min. Eluant was collected as Fractions 1-3 with respective volumes of 10 L, 130 L, and 60 L. The 130 L Fraction 2 was diluted to 450 L with distilled water. The solution was then charged on 50 L of Mitsubishi Diaion HP-20 resin at 4 L/min. The resin was washed first with 150 L of 3:7 methanol-distilled water and then with 80 L of 0.05M potassium phosphate buffer, pH7 in order to convert the absorbed antibiotic complex to the potassium salt form. The resin was washed with 75 L of distilled water and eluted with methanol. Eluant was collected in ten 8 L cuts (Fractions 1-10) and five 19 l cuts (Fractions 11-15). Based on HPLC assay results, Fractions 6 through 15 were combined as the rich cut. The rich cut was concentrated to 2 L. Karl Fisher analysis indicated 62% (by wt.) water. The concentrate was diluted with 540 ml of methanol and 60 ml of 1M potassium phosphate pH7. The sample was charged on a column of 64 L of Diaion HP-20 resin in 85:15 methanol—0.05M potassium phosphate pH7. The resin was first eluted at 250 ml/min with the same solvent (Fractions 1-4, 19 L each; Fractions 5-10, 10 L each) and then eluted at 500 ml/min with 95:5 methanol)—water (Fractions 11-26, 10 L each). Oxydifficidin and oxydifficidin isomer eluted in Fractions 7-14 (combined as Cut 1) while difficidin and difficidin isomer eluted in Fractions 15-23 combined as Cut 2). Cut 2 was combined and concentrated to 720 ml. The sample contained 25 g of difficidin, 2.3 g of the thermal isomer of difficidin and 115 g of total solids. The 720 ml concentrate was diluted with distilled water to 2.2 L, pH6 and adsorbed at 36 ml/min on 1 L of Pharmacia DEAE Sephadex A25, chloride cycle. The resin was washed at 72 ml/min successively with 1 L of 3:7 A25, chloride cycle. The resin was washed at 72 ml/min successively with 1 L of 3:7 methanol-water and 8 L of 9:1 methanol-water. The antibiotic mixture was eluted at the same flow rate with 3% ammonium chloride in 9:1 methanol-water. A series of fifteen 200 ml fractions was collected.

Fractions 3-14 were combined and diluted with sufficient 0.05M potassium phosphate buffer pH7 to lower the methanol concentration to 35%. The slightly cloudy solution was adsorbed on a 1 L column (13 cm ID×7.5 cm) of E. Merck LiChroprep RP-18, 25-40 micron, at 100 ml/min. The resin was washed successively with 4 L of 35:65 methanol—0.05M phosphate buffer pH7.0 and 4.5 L of 45:55 methanol-buffer. The resin was eluted successively with 55:45 methanol-buffer (Fractions 1-8, 500 ml each), 65:35 methanol-buffer (Fractions 9-24, 200 ml each), and 75:25 methanol-buffer (Fractions 25-40, 200 ml each). Difficidin eluted in Fractions 5-25. Fractions 28-37 were enriched in the thermal isomer of difficidin. Combined fractions 28-37, containing 1.2 g of difficidin and 1.8 g of the desired isomer, were diluted with distilled water to a final methanol concentration of 30%. The solution was adsorbed on 200 ml of Mitsubishi Diaion HP-20. After washing the resin with water, the antibiotic was eluted with methanol. Final purification of the thermal isomer of difficidin was performed as follows. The HP-20 rich cut was concentrated to 30 ml and buffered with 2 ml of 1M potassium phosphate pH7. The solution was chromatographed in three equal portions on a Whatman ODS-3M/20 Partisil column (2.1 cm ID×25 cm) equilibrated in 6:4 methanol—0.03M potassium phosphat pH7. The column was eluted at 10 ml/min with 6.4 methanol-buffer over the next 20 minutes followed by a linear gradient from 6.4 to 8.2 methanol-buffer over the next 40 minutes. Appropriate sized fractions were collected and analyzed by HPLC. The rich cuts of the thermal isomer of difficidin from the three runs were combined and desalted in the usual manner on 35 ml of Mitsubishi HP-20 resin. In a similar fashion, the desalted product was again chromatographed in a single portion on a Whatman ODS-3M/20 Partisil column and the resulting rich cut was desalted on 35 ml of HP-20 resin. The final product contained 630 mg of essentially pure thermal isomer of difficidin.

The thermal isomer was lyophilized, which gave a white, amorphous, solid, and then analysed. The results were as follows:

(1) UV Spectrum (in methanol)

| (nm) $\lambda max$ | $A_{1\ cm}^{1\%}$ |
|---|---|
| 234 | 896 |
| 240(sh) | 868 |
| 264(sh) | 284 |
| 273 | 380 |
| 284 | 301 |

(2) Mass Spectral Data

Negative ion fast atom bombardment analysis afforded a strong ion at m/z 543, corresponding to (M-H)−. The molecular weight is therefore 544.

(3) $^1H$ NMR Spectrum

The spectrum is set out in FIG. 1. The spectrum was recorded at 300 MHz in 1:4 $CD_3OD$—$CDCl_3$ at 22° C. Chemical shifts are shown in ppm relative to internal tetramethylsilane zero ppm.

It should be noted that this isolation procedure can also be utilized to isolate the thermal isomer of difficidin produced by MB4488.

EXAMPLE III

Isolation of Oxydifficidin Thermal Isomer from Broth

Cut 1 of Example 2, containing 17 g of oxydifficidin and 7 g of oxydifficidin thermal isomer, is processed in the following way to isolate the thermal isomer. Cut 1 is concentrated to a volume containing approximately 35% by weight of water. The concentrate is diluted with sufficient water to increase the water composition to 70% and adsorbed on 4.5 L of HP-20 resin at 250 ml/min. The resin is washed with 4 L of 3:7 methanol-water and eluted with methanol. Eluate fractions containing oxydifficidin and thermal isomer are combined and concentrated to 455 ml. This solution is chromatographed on 5 L of Sephadex LH-20 resin in methanol at 30 ml/min. The 4 L LH-20 rich cut contains 11 g of oxydifficidin, 5 g of thermal isomer and 36 g of total solids. The rich cut is evaporated to an oily residue, diluted with 150 ml of water and lyophilized. The solid is dissolved to 200 ml in 50:50 methanol—0.05M potassium phosphate pH7 and applied to a 2.2 L column (7 cm ID×57 cm) of LiChroprep RP-18 resin (25-40 micron). After washing the resin with 8 L of the same solvent, oxydifficidin is eluted with 55:45 methanol-buffer. Subsequent elution of the resin with 60:40 methanol-buffer affords oxydifficidin thermal isomer.

Fractions containing the latter are combined, diluted with water to 30% methanol and desalted by absorbing on 500 ml of Amberlite XAD-16 resin. Following a 3:7 methanol-water wash, the desalted thermal isomer is eluted with methanol. The methanol rich cut is concentrated to 50 ml. The final concentrate contains 2.7 g of oxydifficidin thermal isomer mono-potassium salt, contaminated with approximately 5% by weight of the corresponding salt of oxydifficidin.

The thermal isomer is then lyophilized, which gives a white, amorphous, solid substance, and then analyzed. The results are as follows:

(1) UV Spectrum (in methanol)

| (nm) λmax | $A_{1\ cm}^{1\%}$ |
|---|---|
| 235 | 1039 |
| 240(sh) | 1009 |
| 265(sh) | 345 |
| 274 | 456 |
| 285 | 363 |

(2) Mass Spectral Data

Negative ion fast atom bombardment analysis affords a strong ion at m/z 559, corresponding to (M—H)—. The molecular weight is therefore 560.

(3) $^1$H NMR Spectrum

Figure 2:
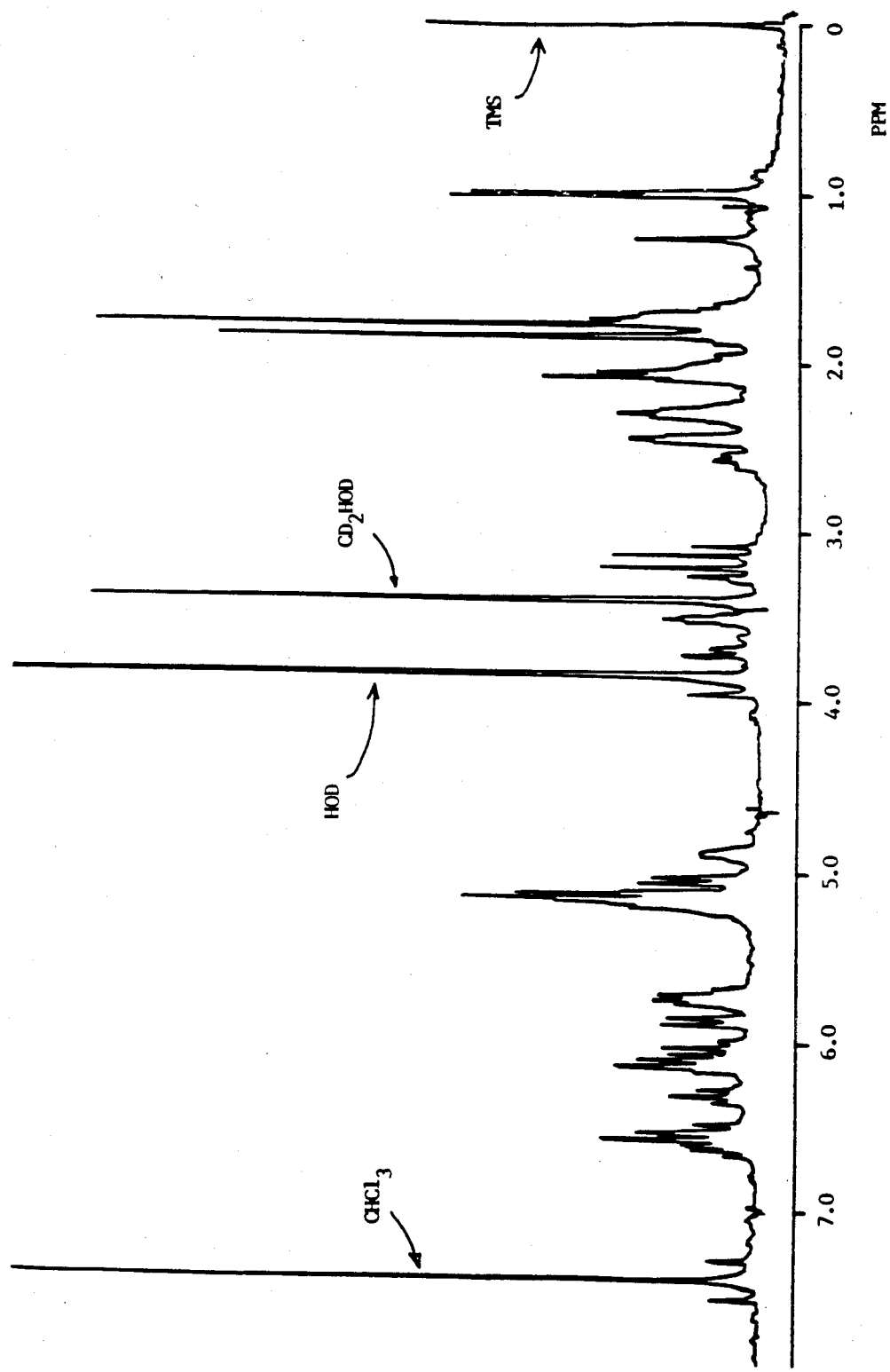

The spectrum is set out in FIG. 2. The spectrum is recorded at 300 MHz in 1:4 CD$_3$OD—CDCl$_3$ at 22° C. Chemical shifts are shown in ppm relative to internal tetramethylsilane zero ppm.

It should be noted that the same isolation procedure can be utilized to isolate the thermal isomer of oxydifficidin made by MB4488.

EXAMPLE IV

Isomerization of Difficidin to Thermal Isomer of Difficidin

Difficidin is stored as the potassium salt at pH7 in aqueous methanol solution at −80° C. A 0.67 ml aliquot containing 400 mcg of difficidin was evaporated to an oil and taken up in 0.2 ml of tetrahydrofuran. The sample was heated at 60° C. for 3 days. HPLC assay results are summarized in Table I.

TABLE I

| | Isomerization of Difficidin to Thermal Isomer of Difficidin at 60° C. | |
|---|---|---|
| | | Composition (1%) |
| Time | Difficidin | Thermal Isomer of Difficidin |
| 0 days | 98% | 2% |
| 3 days | 76% | 24% |

EXAMPLE V

Isomerization of Oxydifficidin to Thermal Isomer of Oxydifficidin

Pure oxydifficidin was stored as the potassium salt, pH7, in aqueous methanol solution at −80° C. A 28 ml aliquot, containing 95 mg of antibiotic, was treated with 2 mg. of 2,6-di-t-butyl-phenol and evaporated to 3-4 ml. The concentrate was diluted with tetrahydrofuran to a final volume of 44 ml. The solution was heated under argon at 60° C. Aliquots were assayed periodically by HPLC and results are summarized in Table 1.

TABLE 1

| | Isomerization of Oxydifficidin to Thermal Isomer of Oxydifficidin at 60° C. | |
|---|---|---|
| | | Composition (96%) |
| Time | Oxydifficidin | Thermal Isomer of Oxydifficidin |
| 0 hrs. | 98 | 2 |
| 17 hrs. | 39 | 61 |
| 24 hrs. | 36 | 64 |
| 41 hrs. | 34 | 66 |

After 41 hrs. at 60° C., the solution was cooled to room temperature and examined by thin layer chromatography on Whatman KC$_{18}$F reverse phase plates using 9:1 methanol-0.1M sodium citrate pH6 as developing solvent. Spots were visualized both by fluorescent quenching under short ultraviolet irradiation and by Hane's Reagents (grey-blue on a white background). The dominant spot with R$_f$=0.75 corresponded to thermal isomer of oxydifficidin while a less intense spot at R$_f$=0.81 coresponded to oxydifficidin. The reaction solution contained 88 mg. of combined oxydifficidin and thermal isomer of oxydifficidin (93% yield) by UV assay.

The product was concentrated to 2 ml and reconstituted to a volume of 4.5 ml containing 30 mM potassium phosphate pH7. This sample was charged on a 95 ml Whatman ODS-3 Partisil M20 10/25 column (2.2 cm ID×25 cm) in 1:1 methanol-30 mM potassium phosphate pH7. The column was eluted at 10 ml/min successively with 62:38 methanol-buffer (Fractions 1–36), 65:35 methanol-buffer (Fractions 37–60), and 70:30 methanol-buffer (Fractions 61–90). All fractions were 20 ml each. Column effluent was monitored at 305 nm. Fractions 46 to 55 were combined as the oxydifficidin rich cut while Fractions 62–77 were combined as the rich cut of the thermal isomer of oxydifficidin. The rich cuts were separately desalted by concentrating each to a volume of 10–15 ml, adsorbing the concentrate on 10 ml of Mitsubishi HP-20 resin at 1 ml/min, washing the resin with 30 ml of 3:7 methanol-water and eluting the antibiotic with methanol. Accordingly, 22 mg of oxydifficidin and 41 mg. of thermal isomer of oxydifficidin were finally obtained. Proton NMR data showed that the thermal isomer of oxydifficidin was identical to the compound isolated in Example III.

What is claimed is:

1. A compound of the formula:

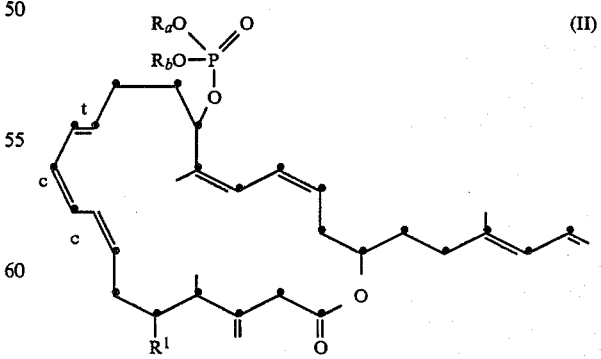

where R$_a$ and R$_b$ are members independently selected from the group consisting of hydrogen, alkali metal and alkaline earth metal cations, ammonium and substituted ammonium and R$^1$ is hydrogen or hydroxy.

2. The compound having a molecular weight of 544, the NMR spectrum of FIG. 1 and the UV spectrum (in methanol):

| (nm) λmax | $A_{1\ cm}^{1\%}$ |
|---|---|
| 234 | 896 |
| 240(sh) | 868 |
| 264(sh) | 284 |
| 273 | 380 |
| 284 | 301 |

3. The compound having a molecular weight of 560, the NMR of FIG. 2 and UV spectrum (in methanol):

| (nm) λmax | $A_{1\ cm}^{1\%}$ |
|---|---|
| 235 | 1039 |
| 240(sh) | 1009 |
| 265(sh) | 345 |
| 274 | 456 |
| 285 | 363 |

4. A pharmaceutical composition for inhibiting the growth of bacteria comprising an antibacterially effective amount of a compound according to claim 1 and a pharmaceutically acceptable carrier.

5. A method of treating bacterial infections in mammals which comprises intravenously, intramuscularly, or subcutaneously administering an antibacterially effective amount of a compound according to claim 1.

* * * * *